United States Patent [19]

Vassiliou

[11] Patent Number: 4,898,020
[45] Date of Patent: Feb. 6, 1990

[54] METHOD AND APPARATUS FOR DETECTING AND ELIMINATING ENTRAPPED GAS BUBBLES IN A THICK FILM COATING

[75] Inventor: Eustathios Vassiliou, Newark, Del.

[73] Assignee: E. I. Du Pont de Nemours and Company, Wilmington, Del.

[21] Appl. No.: 137,098

[22] Filed: Dec. 23, 1987

[51] Int. Cl.$^4$ .............................................. B01D 19/00
[52] U.S. Cl. ........................................... 73/19; 55/55
[58] Field of Search ................... 73/19, 23; 55/55, 189

[56] References Cited

U.S. PATENT DOCUMENTS

| | | | |
|---|---|---|---|
| 4,187,327 | 2/1980 | Lapp et al. | 427/8 |
| 4,293,596 | 10/1981 | Furendal et al. | 427/160 |
| 4,301,189 | 11/1981 | Arai et al. | 427/96 |
| 4,347,302 | 8/1982 | Gotman | 430/270 |
| 4,420,511 | 12/1983 | Liedberg | 427/236 |
| 4,425,376 | 1/1984 | Lee | 427/57 |
| 4,438,159 | 3/1984 | Weber | 427/162 |
| 4,508,756 | 4/1985 | Senda et al. | 427/81 |
| 4,531,959 | 7/1985 | Kar et al. | 65/3.11 |
| 4,636,402 | 1/1987 | Vassiliou | 427/49 |
| 4,647,481 | 3/1987 | Vassiliou | 427/385.5 |

FOREIGN PATENT DOCUMENTS

| | | | |
|---|---|---|---|
| 94605 | 7/1980 | Japan | 55/55 |
| 2097281 | 11/1982 | United Kingdom | 55/55 |

*Primary Examiner*—John Chapman
*Assistant Examiner*—Joseph W. Roskos

[57] ABSTRACT

An entrapped gas bubble in a thick film coating of a member is caused to pulsate when the ambient pressure of the chamber in which the member is disposed is varied. The pulsations may be used to observe the bubble or to cause it to burst.

28 Claims, 1 Drawing Sheet

METHOD AND APPARATUS FOR DETECTING AND ELIMINATING ENTRAPPED GAS BUBBLES IN A THICK FILM COATING

BACKGROUND OF THE INVENTION

1. Field of the Invention

The present invention relates to a method and an apparatus for manufacturing and testing for reliability devices having a coating of a thick film composition thereon and, in particular, to a method and an apparatus for detecting and eliminating entrapped gas bubbles from the coating of the thick film composition.

2. Description of the Prior Art

Because of their high volumetric efficiency and thus their small size multilayer capacitors are the most widely used form of ceramic capacitors for thick film hybrid microelectronic systems. These capacitors are fabricated by stacking and cofiring thin sheets of ceramic substrate on which an appropriate electrode pattern is printed. Each patterned layer is offset from the adjoining layers in such a manner that the electrode layers are exposed alternately at each edge of the assembly. The exposed edges of the electrode pattern are coated with a conductive thick film material to form what is known as the capacitor termination. The termination electrically connects all the layers of the structure, thus forming a group of parallel connected capacitors within the laminated structure. Capacitors of this type are frequently referred to as monolithic capacitors.

During the fabrication of these and other microelectric components that use coatings of thick film compositions it is known that air or other gas bubbles, hereafter collectively referred to as "gas bubbles", may become entrapped within the coating. In the case of the multilayer capacitor, for example, the presence of these gas bubbles may disturb the uniformity of the termination. Although the conductive continuity of the termination is not usually interrupted the high reliability required for most applications does not permit the continued existence of such defects. Thus, from a reliability point of view, the elimination of the entrapped gas bubbles is essential.

Since the formulations used for the terminations are necessarily opaque, containing as they do conducting metals, glass frits and other nontransparent components, it is very difficult to detect the presence of entrapped gas bubbles. In the case of rather large bubbles the coating may develop cracks during drying or firing over the position of the bubble. However, when the size of the gas bubble is small the only way to detect its presence is to dissect the finished device, after the drying and/or the firing thereof, at different positions along the device, in order to ascertain if the devices in a given batch have the entrapped gas bubbles which may lead to defects.

Accordingly, in view of the foregoing it is believed advantageous to provide a method and an apparatus for detecting the presence of entrapped gas bubbles in the coating of the thick film device and, if the bubbles are found to be present, to eliminate or significantly reduce the number of the gas bubbles that are found to be present.

SUMMARY OF THE INVENTION

The apparatus and the method in accordance with the present invention provides an arrangement for detecting and for eliminating entrapped gas bubbles in a thick film composition. In all embodiments the apparatus and the method include a vessel having a chamber therein that is sized to receive one or more members having a coating of a thick film composition thereon. The chamber has a gaseous fluid, such as air, at an initial ambient pressure therein.

In the embodiment wherein the presence of entrapped gas bubbles is detected the vessel is provided with observation means, such as a microscope, by which the member may be observed. Means are provided to vary the pressure of the fluid in the chamber for a predetermined number of cycles between the initial pressure and a second, lower, pressure. Each cycle includes as first period of time during which the fluid in the chamber has the initial pressure followed by a second predetermined time period during which the fluid in the chamber has the second pressure. The initial pressure is substantially atmospheric pressure, while the second pressure less than forty (40) torr, and is preferably less than fifteen (15) torr. The first time period is in the range from 0.1 seconds to two (2) seconds, more preferably in the range from 0.2 to 0.6 seconds, and most preferably 0.4 seconds. The second time is preferably from 0.5 to 10 (10) seconds, more preferably from one (1) to three (3) seconds, and most preferably two (2) seconds. During the cycling the entrapped gas bubbles, if present, will pulsate in a manner that permits their observation through suitable observation means provided on the chamber.

In a second embodiment the vessel and pressure varying means (with or without the observation means) may be used to eliminate entrapped gas from the thick film composition. When the cycling is repeated from two to fifty or more cycles the entrapped gas bubbles may be caused to burst. To assist the elimination of the entrapped gas bubbles it may be desirable in some instances to provide means to saturate the fluid in the chamber with a solvent having a relatively low boiling point less than one hundred twenty (120) degrees Centigrade, and more preferably less than one hundred (100) degrees Centigrade. Useful for such a solvent is 1,1 1 trichloroethane ("chlorothene"). When the low boiling point solvent is used the number of cycles required to eliminate the gas bubbles from the composition is reduced considerably.

In accordance with a further embodiment of the present invention after the cycling the member having the coating of the thick film composition thereon is placed in a chamber of a vessel (either the same or a different vessel, either with or without an observation means) and the ambient fluid in that chamber is saturated with a solvent having a relatively high boiling point in the range from 120 to 350 degrees Centigrade. Suitable for use as such a solvent is beta-terpineol. The member remains in the environment of the chamber for a period of time sufficient to permit gas bubbles therein to be eliminated from the coating. This embodiment of the invention may be used independently of or alternatively to the embodiment wherein the cycling is performed in the environment having a low boiling point solvent. For example, after cycling in a vessel without the low boiling point solvent the member may simply be placed in the environment having the high boiling point solvent therein for a time sufficient to permit the diffusion of the bubbles through and out of the coating. It is noted that if the cycling to eliminate the bubbles is performed without the low boiling point solvent in the chamber.

the high boiling point solvent may be used in the chamber instead to minimize evaporation of the coating during the cycling. Alternately the member may be placed in the environment having the high boiling point solvent as a further step after the member has been cycled in the environment having the low boiling point solvent therein.

It should be understood that in any event wherein a solvent is used to saturate the fluid in the chamber in accordance with the present invention the solvent should be compatible with the liquid component (e.g., the "organic medium" or "vehicle") of the thick film composition.

BRIEF DESCRIPTION OF THE DRAWINGS

The invention will be more fully understood from the following detailed description thereof, taken in connection with the accompanying drawing, which forms a part of this application and in which.

DETAILED DESCRIPTION OF THE INVENTION

The present invention relates to a method and an apparatus for the detection and the elimination of gas bubbles entrapped within the wet and unfired thick film coating of a thick film device. A thick film composition is a dispersion of finely divided particles of electrically functional materials in a liquid vehicle. The composition has a paste-like consistency. Although the invention will be described in terms of the thick film coating used for the termination of multilayer capacitors it should be understood that the invention may be used in the instance of any device having a coating of a thick film composition thereon in which gas bubbles may become entrapped.

Figure 1:
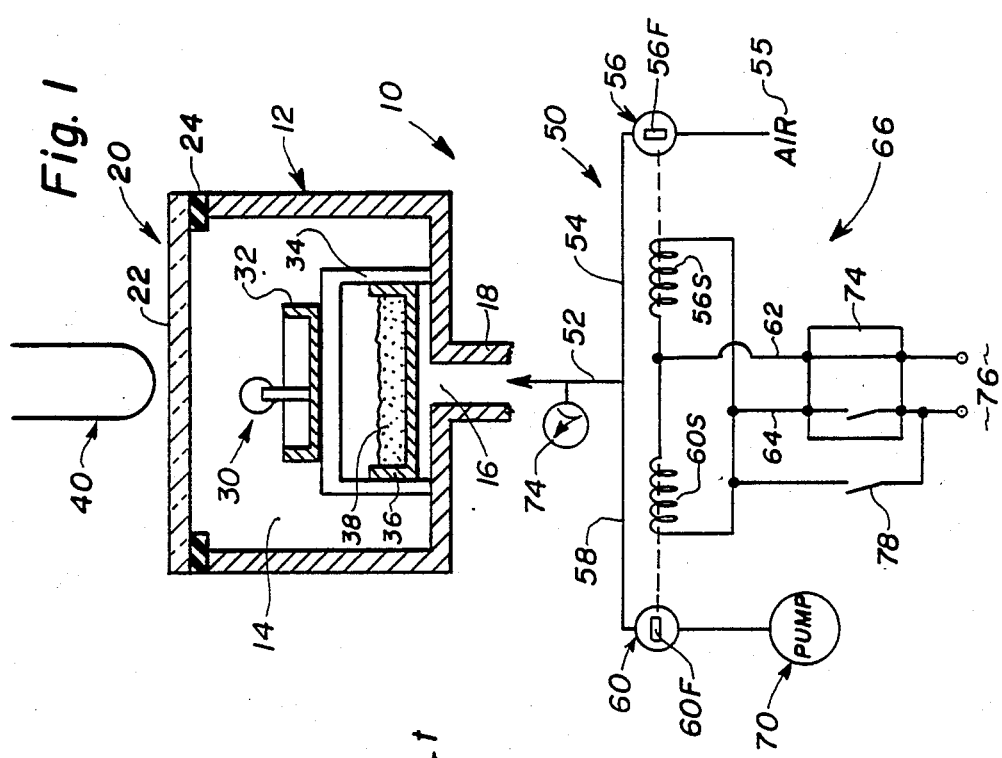
FIG. 1 is a highly stylized schematic representation of an apparatus in accordance with the present invention.

As may be seen from FIG. 1 the apparatus 10 in accordance with the present invention includes a vessel generally indicated by reference 12. The vessel 12 defines an enclosed chamber 14 on the interior thereof. The chamber 14 has therein a gaseous fluid, typically air, although other fluids such as nitrogen may be present therein. At least one port 16 is connected to a pipe 18 whereby communication may be had between a location on the exterior of the vessel 12 and the chamber 14. In the depicted embodiment shown in FIG. 1 the vessel 12 is shown as having an open top but it should be understood that the vessel may be configured in any suitable fashion consistent with the description that follows herein. It should also be understood that the vessel 12 may be fabricated from any suitable material, such as glass, metal or plastic.

The vessel includes a transparent portion 20, such as defined by a viewing window 22. The window 22 is fabricated of glass, transparent plastic or the like. The window 22 is secured to the open top of the vessel 12 in a pressure tight fashion, as by the use of silicone rubber gasket 24 coated with a vacuum grease. The gasket 24 may be fabricated from any suitable resilient gasketing material known in the art, such as rubber. The vacuum grease may be any nonvolatile lubricating paste capable of providing an air-tight interface. Vacuum grease characterized as "heavy" is preferable.

The chamber 14 is sized to define a predetermined volume therein. The volume is sufficient to receive any predetermined number of thick film devices, each of which is generally indicated by the reference character 30. The invention is probably best utilized in a batch mode whereby a plurality of devices are disposed in a tray 32 that is received within the vessel 12. To support the devices 30 on the interior of the vessel 12 a suitable support table 34 is provided in the vessel 12. A cup 36 is disposed in a suitable position on the interior of the vessel 12 for a purpose to be made clear herein. As shown in FIG. 1 the cup 36 is affixed to the support table 34, although such a disposition is not mandated. The cup 36 may be provided with an absorbing material 38, such as a solid foam.

Observation means generally indicated by the reference character 40 is provided in a suitable position with respect to the window 22. The observation means 40 may be configured from any suitable observation device, such as a microscope.

The fluid in the chamber 14 has a predetermined initial pressure therein. Typically the initial pressure is atmospheric pressure. Means generally by reference character 50 are provided to vary the pressure of the fluid in the chamber for a predetermined number of cycles between the initial pressure and a second pressure less than the initial pressure. The means 50 includes a main line 52 connected to the pipe 18 from the vessel 12. A first branch line 54 emanating from a source 55 of gas, such as air, is connected to the main line 52. A valve 56, such as a solenoid controlled valve sold by Goldner Company under model number ASCO 8210C33 is provided in the first line 54. Similarly a second branch line 58 is connected to the main line 52. A second valve 60, similar to the valve 56 but normally closed, such as ASCO 8210C93 sold by Goldner Company, is provided in the second branch line 58. Electrical control lines 62, 64 from a control network 66, to be described, are connected to the solenoids 56S, 60S of the valves 56, 60, respectively. The valves 56, 60 are manufactured by Automatic Switch Company, Florham Park, N.J. The second branch line 58 is connected to a vacuum such as that provided by a house vacuum source or by a vacuum pump 70. If a pump is used care should be taken to use an oil trap, such as a "cold trap," which prevents contamination of the pump by any solvent which may be present in the chamber (as will be discussed). A pressure gauge 74 may be used to monitor the pressure in the main line 52. The valve 56 of the normally open type, as illustrated by the position of the flapper 56F therein, while, conversely, the flapper 60F of the valve 60 is of the normally closed type, as illustrated by the position of its flapper 60F.

The control network 66 includes a timer 74 having a switch 74S therein connected between a source 76 and the solenoids 56S, 60S of the valves 56, 60, respectively. Suitable for use as the timer 74 is a device such as that manufactured and sold by Thomas Scientific Company under model number 451,9373-E65. The timed closure of the switch 74S alternately connects the chamber 14 to the pump 70 and to the air supply 55. An override switch 78 is connected in parallel to the timer 74. The closure of the switch 78 is operative to override the time, and to provide continuous vacuum to the chamber 14 when desired.

Having set forth the interconnection of the basic functional elements of the apparatus of the present invention the operation thereof may now be described.

One or more of the devices 30 having the coating of the thick film composition thereon are disposed in the chamber 14 of the vessel 12. The devices 30 may be carried in the tray 34 or the like set on the table 34. The composition includes, as is well known to those skilled in the art, an "organic medium" or "vehicle." Under the control of the timer-based electrical control network 66 the valves 56, 60 are alternately closed and opened in a manner that varies the pressure of the fluid within the chamber 14. One duty cycle of the pressure variations of the fluid within the chamber 14 is illustrated in FIG. 2.

Figure 2:
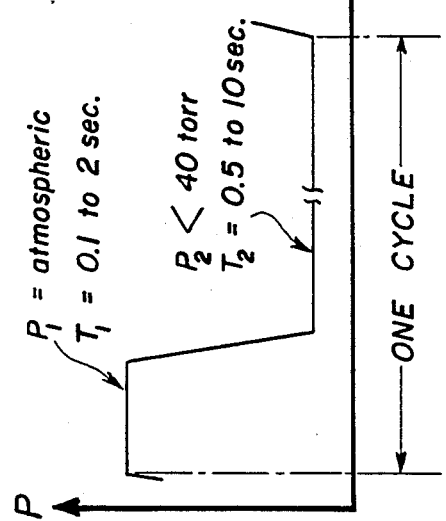
FIG. 2 is a timing diagram illustrating the pressure of the fluid within the vessel of the apparatus shown in FIG. 1.

As seen in FIG. 2 with the initial pressure in the chamber 14 being indicated by the value P1 (preferably equal to atmospheric pressure) the chamber pressure is reduced to the value P2. The pressure P2 is lower than the pressure P1. The pressure P2 is preferably less than forty (40) torr, and more preferably less than fifteen (15) torr, as measured by the gauge 74. The pressure P1 is maintained in the chamber for a first period of time T1 lies in the range from 0.1 seconds to two seconds. Preferably the first time period is in the range from 0.2 seconds to 0.6 seconds, and is most preferably 0.4 seconds. The pressure P2 is maintained in the chamber 14 for the second predetermined time T2. The time period T2 is preferably in the range from 0.5 to ten (10) seconds, more preferably in the range from one (1) second to three (3) seconds, and is most preferably two (2) seconds. It is noted that although the Pressure-time waveform of FIG. 2 approximates a square wave form other waveforms may be used, so long as the minimum and maximum pressures are achieved for the recited time periods. It is also noted that the transition times between the pressures should be abrupt to obtain the desired effect.

The pressure variations are repeated for a predetermined number of cycles, as will be discussed. The pressure variations of the fluid in the chamber 14 permit the detection of the entrapped gas bubbles in the thick film coating of the device 30. During the vacuum portion (T2) of the cycle the entrapped gas bubble expands while it contracts very abruptly during the ambient pressure portion (T1) of the cycle. This causes the bubble to pulsate volumetrically in a manner that is detectable by the observation means 40. The repetitive pressure changes in the fluid in the chamber 14 cause to be formed a very distinct outline of the entrapped gas bubbles that are observable through the means 40. Believed to be one of the main reasons why the gas bubbles are outlined so distinctly during the pressure variations is the fact that the variations give rise to local higher shear-rate conditions in the coating, which in turn decrease the viscosity of the pseudoplastic coating in the immediate vicinity of each of the entrapped gas bubbles. The number of cycles that are necessary before the gas bubbles become visible may vary depending mainly on their position within the coating, on their size, and on the rheological characteristics of the composition. However, in general, the number of cycles is between one (1) and twenty (20) cycles.

The variations in the pressure in the chamber 14 can also be used to cause the bubbles to start breaking totally or partially, converging, or changing their position in the device. The same phenomenon, the local decrease in viscosity, allows the bubbles to move to the surface of the coating, and finally burst and disappear. If the apparatus 10 is used for the purpose of eliminating or reducing the entrapped gas bubbles the transparent portion 20 of the vessel 12 may be omitted, if desired. To eliminate or reduce the entrapped gas bubbles the number of cycles should be in the range from ten (10) to five hundred (500) cycles, more preferably in the range from thirty (30) to one hundred (100) cycles. It should be understood that in any event wherein a solvent is used to saturate the fluid in the chamber in accordance with the present invention the solvent should be compatible with the liquid component (e.g., the "organic medium" or "vehicle") of the thick film composition. Of course, the exact number of cycles will again depend on the position, size and rheological behavior of the thick film composition.

If desired, to retard evaporation of the composition during the pulsing just described it may be desirable to saturate the environment of the chamber 14 with a solvent having a relatively high boiling point, in the range from 120 to 350 degrees Centigrade. Suitable for use as such a solvent is beta-terpineol. It should be understood that the particular solvent chosen is compatible with the vehicle used in the composition. By "compatible" it is meant that the selected solvent has at least limited miscibility into the vehicle. The higher the miscibility, the more compatible is the solvent. The solvent is disposed in the chamber 34 using the cup 36, which thereby provides means to saturate the fluid in the chamber 34 with the solvent.

As an alternative, to further enhance the elimination of the entrapped gas bubbles, in accordance with this invention the fluid in the chamber is saturated using the saturating means defined by the cup 36 with a solvent having a relatively low boiling point. Preferably the boiling point of this solvent is less than one hundred twenty (120) degrees Centigrade and more preferably less than one hundred (100) degrees Centigrade.

Suitable for use as such a low boiling point solvent is 1,1,1 trichloroethane ("chlorothene"), acetone, toluene, methyl ethyl ketone, methanol, heptane, ethyl ether, etc. The preferred solvent is 1,1,1 trichloroethane ("chlorothene") because of its high effectiveness and its nonflammability. By "effectiveness" is meant that this solvent has been found to require the least number of cycles to eliminate bubbles. When the low boiling point solvent is used the number of cycles needed is considerably less than when no solvent (or when the high boiling point) is present. If the low boiling point solvent is used the number of cycles required to eliminate gas bubbles is reduced considerably. It should be noted that when the low boiling point solvent is used the devices should be exposed to the saturated atmosphere for the shortest effective time in order to prevent sagging because the low boiling point solvent tends to decrease the viscosity of the coating, resulting in the sagging of the coating. Of course, if the low boiling point solvent is used, the high boiling point solvent is not used.

In the embodiment of the invention shown in the drawing the means used to saturate the fluid in the chamber 14 used the cup 36 (whether or not the foam member is present) and the disposition of the selected solvent thereinto. Other suitable expedients may be used to saturate the fluid of the chamber. In another embodiment, for example, the member is subjected to the pulsating action until most bubbles migrate to the surface, and the low boiling solvent is then introduced into the chamber for lowering the viscosity of the coating in the vicinity of the surface to burst the bubbles. Yet further, the source 55 may be saturated with the desired solvent, thus eliminating the need for the solvent supply in the chamber. Alternatively, more than one branch 54 and valve 56 may be placed in parallel, each connected to air (or other gas) saturated with the desired solvent.

In accordance with a yet further embodiment of the present invention after the cycling the member having the coating of the thick film composition thereon is placed in a chamber of the vessel (either the same or a different vessel, either with or without the observation means) and the ambient fluid in that chamber is saturated with the relatively high boiling point solvent discussed above. In accordance with this embodiment of the invention the member remains in the environment of the chamber for a period of time sufficient to permit gas bubbles therein to be eliminated by diffusion through and out of the coating. This time period is on the order of a few seconds to a few hours. Of course, this time period is dependent upon the size and position of the bubbles, as well as the composition of the coating. The presence of the high boiling point solvent retards the evaporation of the coating, and thus permits the easier diffusion of entrapped gas bubbles through and out of the coating. It should be understood that this embodiment of the invention may be used independently of or alternatively to the embodiment wherein the cycling is performed in the environment having the low boiling point solvent. For example, after cycling in a vessel without the low boiling point solvent as discussed above (with or without the high boiling point solvent to minimize evaporation) the member may simply be placed in the environment having the high boiling point solvent therein for a time sufficient to permit the diffusion of the bubbles to the surface. Alternately the member may be placed in the environment having the high boiling point solvent as a further step after the member has been cycled in the environment having the low boiling point solvent therein.

Those skilled in the art having the benefit of the teachings of the present invention may impart numerous modifications thereto. For example it lies within the contemplation of the present invention that any other suitable device, whether optical of otherwise, may be used to monitor the pulsations in the coatings of the devices 30 disposed in the chamber 12 and produced in the manner discussed. It is also to be appreciated that the means to vary the pressure in the vessel 12 may be alternately configured. Similarly the arrangement whereby the atmosphere of the chamber is saturated with the particular solvent may differ from that disclosed. Moreover, the time periods, pressures, and solvents may also be varied. These and other modifications are to be construed as lying within the contemplation of the present invention as defined by the present claims.

What is claimed is:

1. Apparatus for detecting the presence of entrapped gas in a coating of a thick film composition disposed on a member comprising:
    a vessel having a chamber sized to receive a member having a thick film composition thereon, the chamber having a fluid therein having an initial ambient pressure,
    observation means for viewing the member within the chamber;
    means for varying the pressure of the fluid in the chamber a predetermined number of cycles between the initial pressure and a second pressure less than the initial pressure to cause any entrapped gas in the thick film composition to pulsate in a manner observable through the observation means,
    wherein each cycle includes a first predetermined time period during which the pressure of the fluid in the chamber is at the initial pressure followed by a second predetermined of time during which the pressure of the fluid in the chamber is at the second pressure,
    wherein, the first time period lies in the range from 0.1 to two seconds and wherein the second time period is in the range from 0.5 to ten (10) seconds, and
    wherein the initial pressure of the fluid in the chamber is atmospheric pressure and wherein the second pressure is less than forty (40) torr.

2. The apparatus of claim 1 wherein first time period lies in the range from 0.2 to 0.6 seconds, wherein the second time period lies in the range from one (1) to three (3) seconds and wherein the second pressure of the fluid in the chamber is less than fifteen (15) torr.

3. A method for detecting the presence of entrapped gas in a coating of a thick film composition disposed on a member comprising the steps of:
    (a) placing a member having a thick film composition thereon in a chamber on the interior of a vessel, the chamber having a fluid therein with an initial ambient pressure therein;
    (b) varying the pressure of the fluid in the chamber a predetermined number of cycles between the initial pressure and a second pressure less than the initial pressure to cause any entrapped gas in the thick film composition to pulsate;
    (c) viewing the member to observe the pulsations of the entrapped gas bubbles;
    wherein each cycle includes a first predetermined time period during which the pressure of the fluid in the chamber is at the initial pressure followed by a second predetermined of time during which the pressure of the fluid in the chamber is at the second pressure,
    wherein, the first time period lies in the range from 0.1 to two (2) seconds and wherein the second time period is in the range from 0.5 to ten (10) seconds, and
    wherein the initial pressure of the fluid in the chamber is atmospheric pressure and wherein the second pressure is less than forty (40) torr.

4. The method of claim 3 wherein the first time period lies in the range from 0.2 to 0.6 seconds, wherein the second time period lies in the range from one (1) to three (3) seconds, and wherein the second pressure of the fluid in the chamber is less than fifteen (15) torr.

5. Apparatus for eliminating entrapped gas in a coating of a thick film composition disposed on a member comprising,
    a vessel having a chamber sized to receive a member having a thick film composition thereon, the chamber having a fluid therein having an initial ambient pressure,
    wherein each cycle includes a first predetermined time period during which the pressure of the fluid in the chamber is at the initial pressure followed by a second predetermined of time during which the pressure of the fluid in the chamber is at the second pressure,
    wherein the first time period lies in the range from 0.1 to two (2) seconds and wherein the second time period is in the range from 0.5 to ten (10) seconds, and wherein the initial pressure of the fluid in the chamber is atmospheric pressure and wherein the second pressure is less than forty (40) torr.

6. The apparatus of claim 5 wherein the first time period lies in the range from 0.2 to 0.6 seconds, wherein the second time period lies in the range from one to three seconds, and wherein the second pressure of the fluid is less than fifteen (15) torr.

7. The apparatus of claim 6 comprising a means for saturating the fluid in the chamber with a solvent having a boiling point in the range from 120 to 350 degrees Centigrade.

8. The apparatus of claim 7 wherein the solvent is beta-terpineol.

9. The apparatus of claim 5 comprising a means for saturating the fluid in the chamber with a solvent having a boiling point in the range from 120 to 350 degrees Centigrade.

10. The apparatus of claim 9 wherein the solvent is beta-terpineol.

11. The apparatus of claim 5 further comprising:
means for saturating the fluid within the chamber with a solvent having a boiling point less than one hundred twenty (120) degrees Centigrade.

12. The apparatus of claim 11
wherein each cycle includes a first predetermined time period during which the pressure of the fluid in the chamber is at the initial pressure followed by a second predetermined of time during which the pressure of the fluid in the chamber is at the second pressure, wherein the first time period lies in the range from 0.1 to two (2) seconds and wherein the second time period is in the range from 0.5 to ten (10) seconds, and wherein the initial pressure of the fluid in the chamber is atmospheric pressure and wherein the second pressure is less than forty (40) torr.

13. The apparatus of claim 12 wherein the first time period lies in the range from 0.2 to 0.6 seconds, wherein the second time period lies in the range from one (1) to three (3) seconds, and wherein the second pressure of the fluid in the chamber is less than fifteen (15) torr.

14. The apparatus of claim 13 wherein the solvent is 1,1,1 trichloroethane.

15. The apparatus of claim 12 wherein the solvent is 1,1,1 trichloroethane.

16. The apparatus of claim 11 wherein the solvent is 1,1,1 trichloroethane.

17. Method for eliminating entrapped gas in a coating on a thick film composition disposed on a member comprising the steps of:
(a) disposing a member having a thick film composition thereon in a chamber having a fluid therein having an initial ambient pressure therein,
(b) varying the pressure of the fluid in the chamber a predetermined number of cycles between the initial pressure and a second pressure less than the initial pressure to cause any bubbles of entrapped gas in the thick film to burst;
wherein each cycle includes a first predetermined time period during which the pressure of the fluid in the chamber is at the initial pressure followed by a second predetermined of time during which the pressure of the fluid in the chamber is at the second pressure, wherein, the first time period lies in the range from 0.1 to two (2) seconds and wherein the second time period is in the range from 0.5 to ten (10) seconds, and wherein the initial pressure of the fluid in the chamber is atmospheric pressure and wherein the second pressure is less than forty (40) torr.

18. The method of claim 17 wherein the first time period lies in the range from 0.2 to 0.6 seconds, wherein the second time period lies in the range from one (1) to three (3) seconds, and wherein the second pressure of the fluid in the chamber is less than fifteen (15) torr.

19. The method of claim 18 further comprising the step of
(c) simultaneously with step b, saturating the fluid within the chamber with a solvent having a boiling point in the range from 120 to 350 degrees Centigrade.

20. The method of claim 19 wherein the solvent is beta-terpineol.

21. The method of claim 17 further comprising:
(c) simultaneously with step (b), saturating the fluid within the chamber with a solvent having a boiling point less than one hundred twenty (120) degrees Centigrade.

22. The method of claim 21 wherein the solvent is 1,1,1 trichloroethane.

23. The method of claim 21 further comprising the step of
(d) following step (c), placing the member in a chamber on the interior of a vessel having a fluid therein saturated with a solvent having a boiling point in the range from 120 to 350 degrees Centigrade; and
(e) removing the member from the chamber after a predetermined time period to permit gas remaining in the composition to migrate to the surface.

24. The method of claim 23 wherein the solvent is beta-terpineol.

25. The method of claim 17 further comprising the step of
(c) following step (b), placing the member in a chamber on the interior of a vessel having a fluid therein saturated with a solvent having a boiling point greater than in the range from 120 to 350 degrees Centigrade; and
(d) removing the member from the chamber after a predetermined time period to permit gas remaining in the composition to migrate to the surface.

26. The method of claim 25 wherein the solvent is beta-terpineol.

27. The method of claim 17 further comprising the step of
(c) simultaneously with step b, saturating the fluid within the chamber with a solvent having a boiling point in the range from 120 to 350 degrees Centigrade.

28. The method of claim 27 wherein the solvent is beta-terpineol.

* * * * *